United States Patent
Tapolsky et al.

(10) Patent No.: US 10,010,542 B2
(45) Date of Patent: Jul. 3, 2018

(54) PFKFB3 INHIBIT AND METHODS OF USE AS AN ANTI-CANCER THERAPEUTIC

(71) Applicant: Advanced Cancer Therapeutics, LLC, Louisville, KY (US)

(72) Inventors: Gilles H. Tapolsky, Louisville, KY (US); Pooran Chand, Birmingham, AL (US)

(73) Assignee: GB ACT, INC., San Diego, CA (US)

(*) Notice: Subject to any disclaimer, the term of this patent is extended or adjusted under 35 U.S.C. 154(b) by 0 days.

(21) Appl. No.: 15/482,956

(22) Filed: May 9, 2017

(65) Prior Publication Data

US 2017/0258783 A1    Sep. 14, 2017

Related U.S. Application Data

(62) Division of application No. 14/388,983, filed as application No. PCT/US2013/031159 on Mar. 14, 2013, now Pat. No. 9,649,305.

(60) Provisional application No. 61/617,073, filed on Mar. 29, 2012.

(51) Int. Cl.
| | | |
|---|---|---|
| *A61K 31/00* | (2006.01) | |
| *A61K 31/724* | (2006.01) | |
| *A61K 31/5377* | (2006.01) | |
| *A61K 31/4709* | (2006.01) | |
| *C07D 401/06* | (2006.01) | |
| *A61K 45/06* | (2006.01) | |
| *A61K 9/08* | (2006.01) | |
| *A61K 9/19* | (2006.01) | |
| *A61K 47/26* | (2006.01) | |
| *A61K 47/40* | (2006.01) | |

(52) U.S. Cl.
CPC .......... *A61K 31/4709* (2013.01); *A61K 9/08* (2013.01); *A61K 9/19* (2013.01); *A61K 31/00* (2013.01); *A61K 45/06* (2013.01); *A61K 47/26* (2013.01); *A61K 47/40* (2013.01); *C07D 401/06* (2013.01)

(58) Field of Classification Search
None
See application file for complete search history.

(56) References Cited

U.S. PATENT DOCUMENTS

| | | | |
|---|---|---|---|
| 7,034,013 B2 * | 4/2006 | Thompson | A61K 9/0019 514/58 |
| 8,088,385 B2 | 1/2012 | Chesney et al. | |
| 2009/0074884 A1 * | 3/2009 | Chesney | A61K 31/00 424/649 |

OTHER PUBLICATIONS

Foye's Principles of Medicinal Chemistry ("Foye", Lippincott Williams & Wilkins Philadelphia, 2002, 59-63).*
Clem et al, "Small-molecule inhibition of 6-phosphofructo-2-kinase activity suppresses glycolytic flux and tumor growth," Molecular Cancer Therapeutics, American Assoc of Cancer Research, 7(1): 110-120, Jan. 1, 2008.
Foye's Principles of Medicinal Chemistry, ("Foye", Lippincott Williams & Wilkins Philadelphia, 2002, 59-63).
Seo et al, "Structure-Based Development of Small Molecule PFKFB3 Inhibitors: A Framework for Potential Cancer Therapeutic AGents Targeting the Warburg Effect," Pios ONE 6(9), E24179, pp. 1-12, 2011.

* cited by examiner

*Primary Examiner* — Misook Yu
*Assistant Examiner* — Kauser M Akhoon
(74) *Attorney, Agent, or Firm* — Dinsmore & Shohl LLP

(57) ABSTRACT

A novel compound, (E)-1-(pyridyn-4-yl)-3-(7-(trifluoromethyl)quinolin-2-yl)-prop-2-en-1-one, is provided herein. (E)-1-(pyridyn-4-yl)-3-(7-(trifluoromethyl)quinolin-2-yl)-prop-2-en-1-one is an inhibitor of 6-phosphofructo-2-kinase/fructose-2,6-biphosphatase 3 (PFKFB3) with surprisingly superior efficacy and pharmacodynamic properties in vitro and in vivo. Also provided are pharmaceutical compositions including the compound and methods of use of the compound in treating cancer and tumors in vivo, as well as inhibiting glycolytic flux and PFKFB3 enzymatic activity in cells.

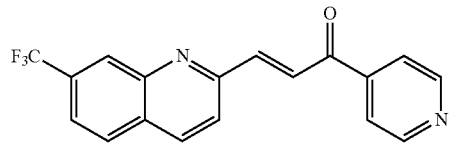

11 Claims, 8 Drawing Sheets

PFKFB3 INHIBIT AND METHODS OF USE AS AN ANTI-CANCER THERAPEUTIC

CROSS-REFERENCE TO RELATED APPLICATIONS

This application is a divisional of U.S. application Ser. No. 14/388,983 filed on Sep. 29, 2014, which is a § 371 of International Application No. PCT/US2013/031159 filed on Mar. 14, 2013, and which claims the benefit of U.S. Provisional Application Ser. No. 61/617,073, filed on Mar. 29, 2012, the entire disclosures of which are incorporated herein by this reference.

TECHNICAL FIELD

The presently disclosed subject matter relates to a novel anti-cancer agent, (E)-1-(pyridyn-4-yl)-3-(7-(trifluoromethyl)quinolin-2-yl)-prop-2-en-1-one, as an inhibitor of 6-phosphofructo-2-kinase/fructose-2,6-biphosphatase 3 (PFKFB3) and methods of using the same to treat cancer and tumors in mammals, including humans.

BACKGROUND ART

The glycolytic pathway is a ten-step series of reactions that forms the major metabolic pathway in nearly all organisms. Flux through the glycolytic pathway is adjusted in response to conditions both inside and outside the cell. Irreversible glycolytic reactions are those catalyzed by hexokinase, phosphofructokinase, and pyruvate kinase. In metabolic pathways, such enzymes are potential targets for control, and all three enzymes serve this purpose in glycolysis. The PFKFB enzymes (PFKFB 1-4) synthesize fructose-2,6-bisphosphate (F2,6BP) which activates 6-phosphofructo-1-kinase (PFK-1), an essential control point in the glycolytic pathway.

Neoplastic cells preferentially utilize glycolysis to satisfy their increased needs for energy and biosynthetic precursors. Malignant tumor cells have glycolytic rates that are up to 200 times higher than those of their normal tissues of origin. One cancer attack strategy has been to treat cancer by starving cancerous cells in various ways. Reducing or blocking the enhanced glycolytic flux mechanism present in cancer cells has stimulated recent interest.

Despite greater understanding and pharmaceutical advances in the diagnosis and treatment of cancer, it is still estimated that nearly 13% of all human deaths last year were due to cancer. Thus, there remains a need for safe and effective anti-cancer therapeutics, particularly those which target neoplastic cells via mechanisms such as glycolytic flux, which are over-expressed in cancer cells.

SUMMARY OF INVENTION

Provided herein is a PFKFB3 inhibitor that has demonstrated unexpectedly superior in vitro properties, in vivo pharmacokinetic properties, in vivo tolerability and safety data, and in vivo inhibition of tumor growth as compared to quinolyl-propenone derivatives described previously.

In one embodiment, a compound for the treatment of cancer is provided, consisting of (E)-1-(pyridyn-4-yl)-3-(7-(trifluoromethyl)quinolin-2-yl)-prop-2-en-1-one, or a pharmaceutically acceptable salt thereof, having the formula:

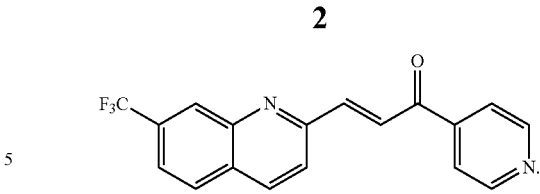

In another embodiment, a pharmaceutical composition for the treatment of cancer is provided, comprising:
(a) an effective amount of (E)-1-(pyridyn-4-yl)-3-(7-(trifluoromethyl)quinolin-2-yl)-prop-2-en-1-one or a pharmaceutically acceptable salt thereof; and
(b) at least one pharmaceutically acceptable carrier.

In another embodiment, a method of treating cancer is provided, the method comprising administering to a subject in need thereof an effective amount of (E)-1-(pyridyn-4-yl)-3-(7-(trifluoromethyl)quinolin-2-yl)-prop-2-en-1-one or a pharmaceutically acceptable salt thereof.

In another embodiment, a method of treating a tumor is provided, the method comprising administering to a subject in need thereof an effective amount of (E)-1-(pyridyn-4-yl)-3-(7-(trifluoromethyl)quinolin-2-yl)-prop-2-en-1-one or a pharmaceutically acceptable salt thereof.

In still another embodiment, a method of inhibiting glycolytic flux in a cell is provided, the method comprising contacting the cell with an effective amount of (E)-1-(pyridyn-4-yl)-3-(7-(trifluoromethyl)quinolin-2-yl)-prop-2-en-1-one or a pharmaceutically acceptable salt thereof.

In another embodiment, a method of inhibiting enzymatic activity of PFKFB3 in a cell is provided, the method comprising contacting the cell with an effective amount of (E)-1-(pyridyn-4-yl)-3-(7-(trifluoromethyl)quinolin-2-yl)-prop-2-en-1-one or a pharmaceutically acceptable salt thereof.

These and other objects, features, embodiments, and advantages will become apparent to those of ordinary skill in the art from a reading of the detailed descriptions. All percentages, ratios and proportions herein are by weight, unless otherwise specified. All temperatures are in degrees Celsius (° C.) unless otherwise specified.

DESCRIPTION OF EMBODIMENTS

Figure 1:
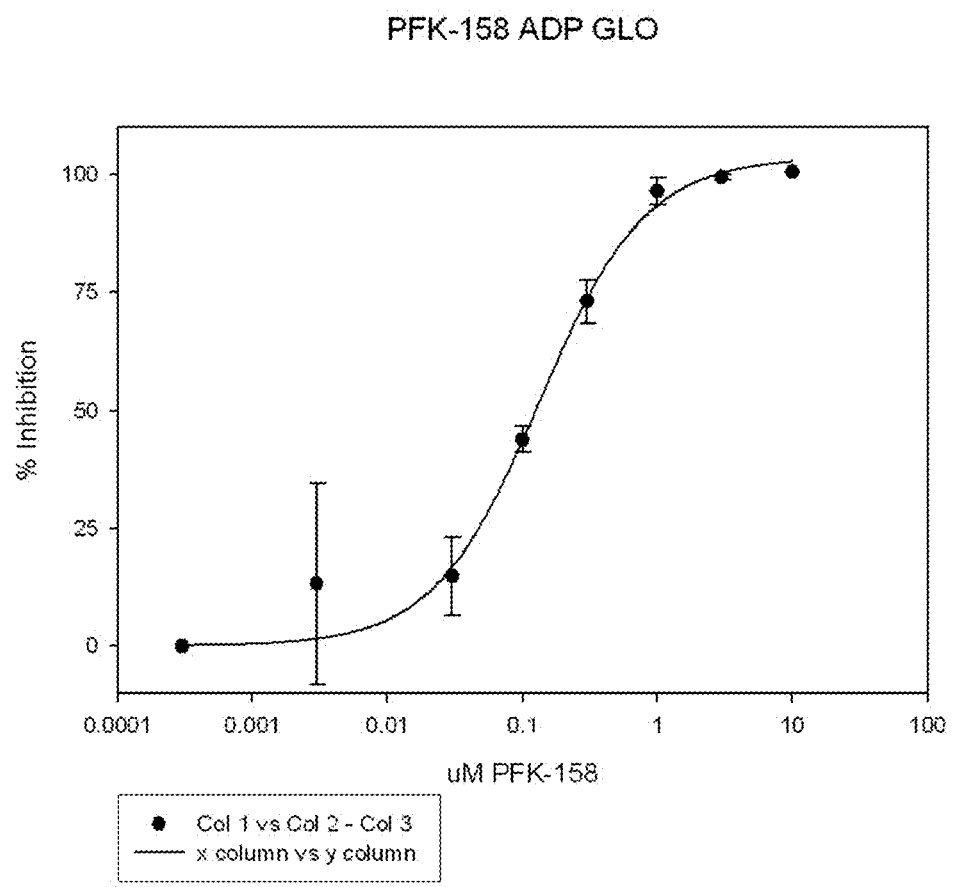
FIG. 1 shows inhibition of the enzymatic activity of PFKFB3 vs. concentration for PFK-158 (ADP-Glo™ assay).

The details of one or more embodiments of the presently-disclosed subject matter are set forth in this document. Modifications to embodiments described in this document, and other embodiments, will be evident to those of ordinary skill in the art after a study of the information provided in this document.

While the following terms are believed to be well understood by one of ordinary skill in the art, definitions are set forth to facilitate explanation of the presently disclosed subject matter.

Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

The term "cancer" as used herein refers to diseases caused by uncontrolled cell division and the ability of cells to metastasize, or to establish new growth in additional sites. The terms "malignant," "malignancy," "neoplasm," "tumor," and variations thereof refer to cancerous cells or groups of cancerous cells.

The term "anti-cancer agent," "anti-cancer compound," "anti-neoplastic compound," "anti-tumor agent," "anti-cancer therapeutic" and variations thereof as used herein refer to compounds that can prevent the proliferation of cancer cells and tumors or kill cancer cells.

Specific types of cancer include, but are not limited to, glioblastoma multiforme, skin cancers, connective tissue cancers, adipose cancers, breast cancers, lung cancers, stomach cancers, pancreatic cancers, ovarian and reproductive organ cancers, cervical cancers, uterine cancers, anogenital cancers, kidney cancers, bladder cancers, liver cancers, colorectal or colon cancers and digestive (GI) tract cancers, prostate cancers and reproductive organ cancers, central nervous system (CNS) cancers, retinal cancer, blood, and lymphoid cancers, and head and neck cancers.

6-phosphofructo-2-kinase/fructose-2,6-biphosphatase 3, or PFKFB3, is a molecular target for the development of anti-cancer therapeutics. It has now been discovered that the PFKFB3 inhibitor (E)-1-(pyridyn-4-yl)-3-(7-(trifluoromethyl)quinolin-2-yl)-prop-2-en-1-one possesses unexpectedly superior properties as compared to previously described quinolyl-propenones.

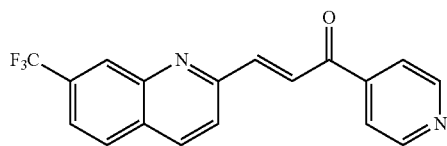 [SMILES: O=C(/C=C/c1ccc2ccc(C(F)(F)F)cc2n1)c1ccncc1]

(E)-1-(pyridyn-4-yl)-3-(7-(trifluoromethyl)quinolin-2-yl)-prop-2-en-1-one (PFK-158)

(E)-1-(pyridyn-4-yl)-3-(7-(trifluoromethyl)quinolin-2-yl)-prop-2-en-1-one, also referred to interchangeably herein as PFK-158, exhibits unpredicted superior efficacy in vitro against the target protein PFKFB3 and cancer cells, and superior pharmacodynamics, safety, and efficacy in vivo in tumor inhibition.

1-pyridin-3-yl-3-quinolin-3-yl-propenone has been disclosed in U.S. Pat. No. 8,088,385, issued Jan. 3, 2012 to Chesney, et al. This compound, also referred to as PFK-015, exhibits demonstrated efficacy in mouse studies of tumor treatment.

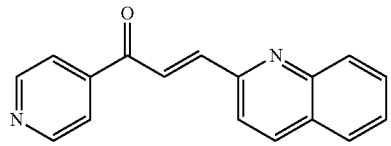 [SMILES: O=C(/C=C/c1ccc2ccccc2n1)c1ccncc1]

1-pyridin-3-yl-3-quinolin-3-yl-propenone (PFK-015)

PFK-158 differs from PFK-015 by the addition of a trifluoromethyl substituent on the 7-position of the quinoline ring. However, pharmaceutical properties of PFK-015, such as solubility and stability in pharmaceutical solvents generally recognized as safe for parenteral administration to cancer patients, render that compound unsuitable for use in treating cancer patients.

Studies suggest that, despite structural similarities with PFK-015, the instantly disclosed compound exhibits surprisingly superior in vitro properties, in vivo pharmacokinetic properties, in vivo tolerability and safety properties, and in vivo inhibition of tumor growth. Overall, these unexpected superior properties indicate PFK-158 is a relatively safe and effective treatment of cancer and autoimmune diseases.

In vitro data comparing PFK-158 with PFK-015 shows that PFK-158 exhibits superior potency in inhibiting PFKFB3 enzymatic activity, inhibiting 2 deoxyglucose uptake, and killing cancer cells in vitro. See Table 1 below.

TABLE 1

Comparative $IC_{50}$ data for PFK-158 vs. PFK-015

| Compound | $IC_{50}$, Enzymatic activity of PFKFB3, ADP Glo™ Assay[1] | $IC_{50}$, Enzymatic activity of PFKFB3 in cells[2] | $IC_{50}$, Inhibition of 2 deoxyglucose uptake[3] | $IC_{50}$, toxicity of Jurkat cell line (leukemia cell line)[4] |
|---|---|---|---|---|
| ![PFK-158] | 137 ± 15 nM | 1.6 ± 0.8 μM | 0.8 ± 0.1 μM | 0.33 ± 0.1 μM |

TABLE 1-continued

Comparative IC$_{50}$ data for PFK-158 vs. PFK-015

| Compound | IC$_{50}$, Enzymatic activity of PFKFB3, ADP Glo™ Assay[1] | IC$_{50}$, Enzymatic activity of PFKFB3 in cells[2] | IC$_{50}$, Inhibition of 2 deoxyglucose uptake[3] | IC$_{50}$, toxicity of Jurkat cell line (leukemia cell line)[4] |
|---|---|---|---|---|
| PFK-015 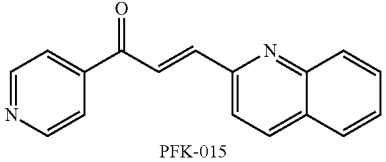 | 318 ± 19 nM | 4.7 ± 1.6 µM | 1.2 ± 0.1 µM | 0.8 ± 0.1 µM |

[1]Determined using commercially available ADP Glo™ Assay kit (Promega, Madison, WI)
[2]PFKFB3 inhibition is measured in cells by measuring fructose-2,6-bisphosphonate levels according to the method of Van Schaftingen (Eur. J. Biochem. 129:191 (1982)). See Example 2 for experimental conditions.
[3]Inhibition of PFKFB3 in cells results in inhibiting glucose uptake by cells. An assay was developed to determine the concentration inhibiting cellular uptake. See Example 2 for experimental details.
[4]See Example 1 for experimental details.

Table 1 results illustrate that, surprisingly, the compound of the invention exhibits two-fold or nearly two-fold superior efficacy, when compared to the structurally similar PFK-015.

Furthermore, PFK-158 also exhibits unexpected and superior pharmacokinetic properties. As shown in Table 2, key pharmacokinetic parameters obtained in Balbc mice of the compound of the invention, such as T$_{1/2}$ (half-life), C$_{max}$ (maximum concentration), AUC (area under the curve), or Cl (clearance), show that PFK-158 exhibits unpredicted and superior pharmacokinetics compared to PFK-015 administered at the same concentration (IV dosing). PFK-158 exhibits a higher C$_{max}$ and AUC, longer half-life, and lower clearance compared to PFK-015.

TABLE 2

Pharmacokinetic Parameters

| Compound | T$_{1/2}$ (hr) | C$_{max}$ (ng/ml) | AUC$_{0-Inf}$ (ng · h/mL) | Cl (mL/min/kg) |
|---|---|---|---|---|
| 1-(pyrydin-4-yl)-3-(7-(trifluoromethyl) quinolin-2-yl) prop-2-en1-one (PFK-158) | 10.5 | 4176 | 3235 | 26 |
| 1-Pyridin-4-yl-3-(quinolin-2-yl)-propenone (PFK-015) | 5.0 | 3053 | 1804 | 46 |

Further, the in vitro stability of the above compounds in human liver microsomes as a function of time illustrates that the compound of the invention is unexpectedly and significantly more stable (a near two-fold improvement in stability). See Table 3, below.

TABLE 3

Percent metabolized after 1 hr in human liver microsomes

| Compound | Percent metabolized after 1 hr |
|---|---|
| 1-(pyrydin-4-yl)-3-(7-(trifluoromethyl) quinolin-2-yl) prop-2-en1-one (PFK-158) | 37% |
| 1-Pyridin-4-yl-3-(quinolin-2-yl)-propenone (PFK-015) | 67% |

Several maximum tolerated dose studies and toxicology studies were performed and the results indicated PFK-158 is safer than PFK-015. Studies were performed in C57/Bl6 mice and SD rats. Maximum Tolerated Doses (MTDs) were determined by either a body weight loss superior to 10% or death of animals during the study using a 3 days on/3 days off schedule. For PFK-158, the MTD was not reached and was thus defined as >45 mg/kg, while the MTD for PFK-015 was significantly lower, at 30 mg/kg. See Table 4, below.

TABLE 4

Maximum tolerated dose (MTD)

| Compound | MTD |
|---|---|
| 1-(pyrydin-4-yl)-3-(7-(trifluoromethyl) quinolin-2-yl) prop-2-en1-one (PFK-158) | Not reached, >45 mg/kg |
| 1-Pyridin-4-yl-3-(quinolin-2-yl)-propenone (PFK-015) | 30 mg/kg |

Toxicology studies were performed in SD rats comparing PFK-158 and PFK-015 using a repeat dosing schedule. The studies were performed at dose levels ranging from 5 to 30 mg/kg and animals were monitored for weight loss, behavior, clinical signs, and clinical chemistries. At the end of the study, gross pathology and histopathology were performed. There were no adverse observations for PFK-158 for any of the tests performed, indicating that PFK-158 was very well tolerated and that the MTD would be higher than 30 mg/kg. The same study was conducted for PFK-015 at 2 dose levels (12 and 25 mg/kg), and adverse observations at both dose levels included body weight loss, decrease food consumption, clinical lethargy, increase in leukocyte, lymphocyte and neutrophil counts, macroscopic and microscopic findings, clinical pathology findings, and death. Based on these results, the MTD for PFK-015 in rats was determined to be 12 mg/kg. The difference in MTD values between the two compounds is unexpected and was not predicted from the pharmacokinetic profiles. Toxicology studies indicate PFK-158 is significantly safer than the structurally similar PFK-015.

Studies determining efficacy of PFK-158 at inhibiting tumor growth in mouse cancer models were performed. These studies were carried out with PFK-158 alone and in combination with compounds currently used in the treatment of cancer patients. Studies were performed in a lung cancer model, a pancreatic cancer model, and in a colon cancer model. In each case, the compound of the invention exhibited significant activity with tumor growth inhibition ranging from 50% to 70%, anti-tumor activity comparable to the controls used in those studies (chemotherapeutic agents used clinically to treat these tumor types such as paclitaxel, gemcitabine, and irinotican), without noticeable body weight loss or death (see Example 4 and FIGS. 6-8). Animals treated with PFK-015 exhibited similar activity but treatment was not as well tolerated, as body weight loss higher than 15% was observed, together with other clinical observations indicating adverse side effects. PFK-158 is better tolerated and safer than the structurally similar PFK-015. This tolerability benefit is significant, as it allows the combination of different anti-cancer compounds to increase tumor growth inhibition without increasing lethal side effects that minimize the benefits of such combinations.

Further, the solubility properties of PFK-158 are such that, if required, the compound can be administered using either a phospho-lipidic aqueous based emulsion, or in an emulsifier-free, solvent-free aqueous based solution. Surprisingly, the compound according to the invention does not, in the formulation mentioned above, undergo a rapid photoisomerization in these solutions. Hence, the unexpected added benefit simplifies administration to patients suffering from cancer or an autoimmune disease and does not necessarily require amber tubings or over-pouches to reduce UV exposure.

I. Compound

In one embodiment, the compound (E)-1-(pyridyn-4-yl)-3-(7-(trifluoromethyl)quinolin-2-yl)-prop-2-en-1-one is provided, having the following structural formula:

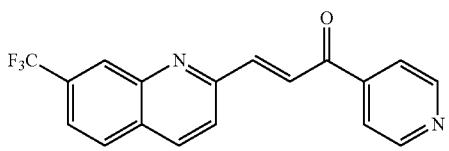 [SMILES: O=C(/C=C/c1ccc2ccc(C(F)(F)F)cc2n1)c1ccncc1]

and includes any pharmaceutically acceptable salts, isomers, prodrugs, or metabolites thereof.

II. Chemical Synthesis (E)-1-(pyridyn-4-yl)-3-(7-(trifluoromethyl)quinolin-2-yl)-prop-2-en-1-one, or PFK-158, is prepared using the general methods described below in Schemes I or II, together with synthetic methods known to those skilled in the art of organic synthesis and variations thereon.

As briefly described in the schemes below, the compound of the invention can be prepared by the reaction of the corresponding quinoline aldehyde with the corresponding unsubstituted acetyl derivative in the presence of a suitable base. Alternatively, the aldehyde may also be reacted with phosphorylidene derivative to give the desired product.

Two detailed synthetic schemes for the preparation of compound of the invention are described below.

Scheme 1:

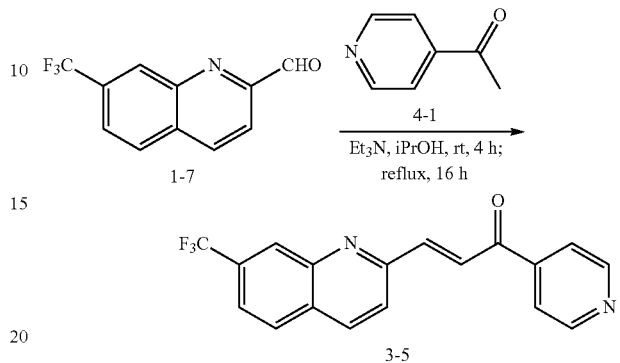

Preparation of 1-Pyridin-4-yl-3-[7-trifluoromethyl) quinolin-2-yl]prop-2-en-1-one (3-5)

Triethyl amine (0.96 mL, 6.6 mmol, 0.5 eq) was added to the mixture of 7-(trifluoromethyl)quinoline-2-carbaldehyde (1-7) (3 g, 13.32 mmol) and 4-acetylpyridine (4-1) (1.93 g, 15.98 mmol, 1.2 eq.) in isopropyl alcohol (75 mL) at room temperature. The reaction mixture was stirred at room temperature for 4 h then heated at reflux for 16 h. The reaction mixture was concentrated to 35 mL and cooled to 0° C. The precipitated product was collected by filtration, washed well with chilled isopropyl alcohol (5×2 mL) and dried under vacuum to give compound 3-5 (1.47 g, 33%). $^1$H NMR (300 MHz, DMSO-d$_6$): δ 8.90 (d, J=5.40 Hz, 2H), 8.66 (d, J=8.70 Hz, 1H), 8.42-8.36 (m, 2H), 8.33-8.26 (m, 2H), 8.02 (d, J=5.40 Hz, 2H), 7.95-7.87 (m, 2H). HPLC purity (area %): 100% in 1000 ppm in DMSO.

Scheme 2:

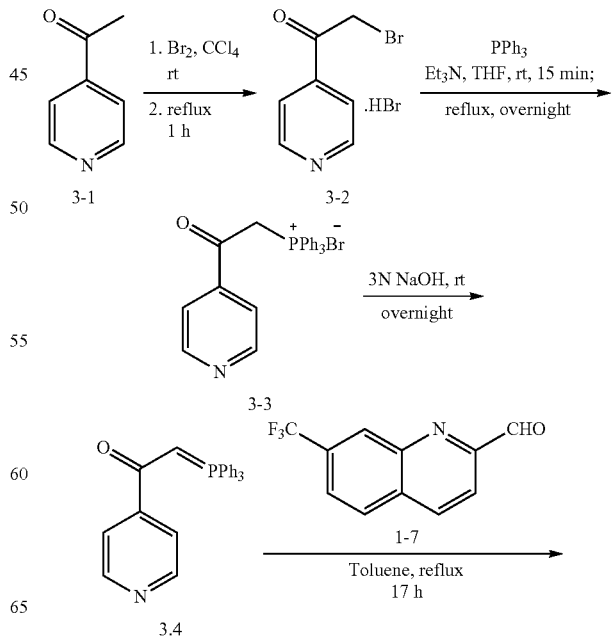

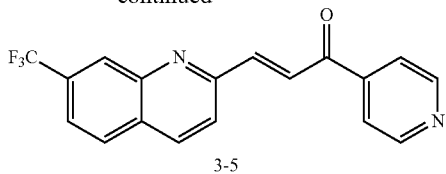

3-5

Preparation of 2-bromo-1-pyridin-4-yl-ethanone hydrobromide (3-2)

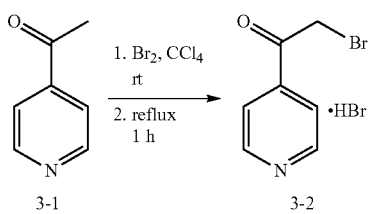

Bromine (131.92 g, 825.49 mmol) was added slowly at room temperature to a stirred solution of 3-1 (100 g, 825.491 mmol) in CCl$_4$ (2.5 L). The reaction mixture was then heated slowly to reflux for 1 h [reaction is exothermic and may be vigorous once it reaches 72° C.]. The product was precipitated out as light yellow solid. The reaction mixture was then cooled to room temperature and the product was collected by filtration, washed three times with diethyl ether (1.5 L in total) and dried to obtain compound 3-2 (234.6 g).

Preparation of (2-oxo-2-pyridin-4-yl-ethyl)-triphenyl-phosphonium bromide (3-3)

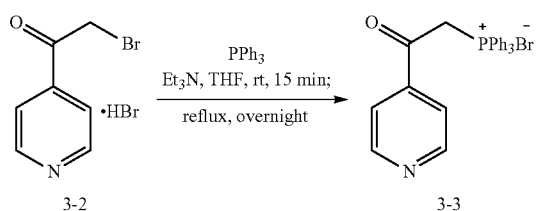

Triphenyl phosphine (219.46 g, 836.72 mmol) in deoxygenated THF (5 L) was added at room temperature in six equal portions to a fine suspension of 3-2 (234 g, 835.05 mmol) in THF (2 L) under a nitrogen atmosphere. Triethyl amine (84.49 g, 835.05 mmol) was then added at room temperature and the resulting mixture was stirred for 15 min at room temperature and then was heated at reflux overnight with vigorous stirring. The reaction mixture was then cooled to room temperature. The precipitated light brown solid was collected by filtration, washed three times with diethyl ether (1.5 L in total) and dried to give compound 3-3 (385.85 g).

Preparation of 1-pyridin-4-yl-2-(triphenyl-λ$^5$-phosphanylidene)ethanone (3-4)

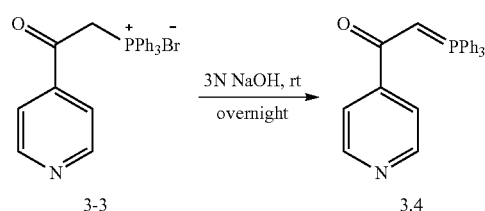

3N Aqueous sodium hydroxide solution (2.85 L) was added slowly at room temperature to a solution of 3-3 (385.85 g, 834.59 mmol) in mixed solvent system of methanol (0.762 L) and distilled water (1.43 L) and the reaction mixture was stirred overnight at room temperature. The methanol was evaporated under reduced pressure and the resulting product in the aqueous residue was collected by filtration, washed with distilled water (2 L) and diethyl ether (1.5 L) and dried to give the product 3-4 (115 g, 36%) as a brown solid.

Preparation of 1-pyridin-4-yl-3-[7-(trifluoromethyl)quinolin-2-yl]prop-2-en-1-one (3-5)

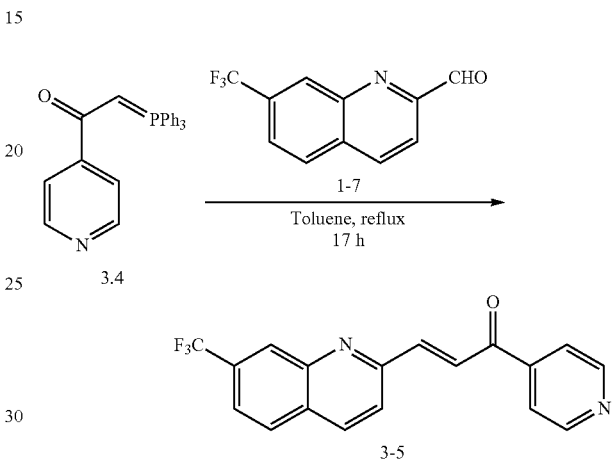

7-(Trifluoromethyl)quinoline-2-carbaldehyde 1-7 (50 g, 222 mmol) was added at room temperature to a solution of 3-4 (84.6 g, 0.222 mol) in toluene (1 L). The reaction mixture was slowly heated to reflux and maintained under reflux for 17 h (the progress of the reaction was monitored by TLC and mass spectroscopy). The toluene was distilled off under reduced pressure and the residue was crystallized from warm ethanol give pure 3-5 (46.14 g, 63.3%). MS calculated for $C_{18}H_{14}N_2O_2$ (M+H$^+$) 329.3 was found 329.3. $^1$H NMR (300 MHz, DMSO-d$_6$): δ 8.90 (d, J=5.40 Hz, 2H), 8.66 (d, J=8.70 Hz, 1H), 8.42-8.36 (m, 2H), 8.33-8.26 (m, 2H), 8.02 (d, J=5.40 Hz, 2H), 7.95-7.87 (m, 2H). HPLC purity 99.74% (area %).

III. Pharmaceutical Compositions (E)-1-(pyridyn-4-yl)-3-(7-(trifluoromethyl)quinolin-2-yl)-prop-2-en-1-one (PFK-158), including pharmaceutically acceptable salts thereof, can be administered to a subject either alone, or as part of a pharmaceutical composition.

Pharmaceutical compositions comprising PFK-158 are also provided herein. These pharmaceutical compositions comprise PFK-158 in a pharmaceutically acceptable carrier. Pharmaceutical formulations can be prepared for intravenous or parenteral administration, as discussed in greater detail below. Also, PFK-158 can be reconstituted to form pharmaceutically acceptable compositions (including compositions pharmaceutically acceptable in humans) for administration.

The term "carrier," as used herein, includes pharmaceutically acceptable carriers, excipients, or stabilizers which are nontoxic to the cell or mammal being exposed thereto at the dosages and concentrations employed.

The therapeutically effective dosage of PFK-158, the use of which is within the scope of embodiments described herein, will vary somewhat from subject to subject and will depend upon the condition of the subject and the route of delivery. As a general proposition, a dosage from about 0.1 to about 500 mg/kg will have therapeutic efficacy, with all weights being calculated based upon the weight of the active compound, including the cases where a salt is employed.

In accordance with the presently disclosed methods, PFK-158 can be administered intramuscularly, subcutaneously, intra-arterially, or intravenously as a solution, suspension, or emulsion. Alternatively, the compound or its salts can also be administered intravenously, intra-arterially, or intramuscularly as a liposomal suspension.

Pharmaceutical compositions suitable for intravenous or intramuscular injection are further embodiments provided herein. If a solution is desired, water is the carrier of choice. With respect to the water-based solutions, an emulsifier and or a pharmaceutically acceptable organic vehicle, such as glycerol, propylene glycol, polyethylene glycol, or mixtures thereof, can be suitable. If an emulsifier is required to keep the solution or emulsion stable, then emulsifiers such as, but not limited to, derived from polyethoxylated castor oil and known as Cremophor®, RH 40 Cremophor® and all their derivatives, from polyethoxylated sorbitan and oleic acid and known as Tween 60 or 80®, Polysorbate 60 or 80® and all their derivatives, from alpha-tocopherol and derivatives, can be suitable. The use of molecules forming inclusion complexes like cyclodextrin, such as Captisol® or Kleptose®, allows obtaining water based formulation without solvents or emulsifiers. In either instance, prepared solutions can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to the compound of the invention, including its pharmaceutically acceptable salts thereof, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical compositions described herein can be lyophilized using techniques well known in the art.

In yet another embodiment there is provided an injectable, stable, sterile formulation comprising PFK-158 or a pharmaceutically acceptable salt thereof, in a unit dosage form in a sealed container. The compound is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt.

Additional embodiments provided herein include liposomal formulations of the active compound disclosed herein. The technology for forming liposomal suspensions is well known in the art.

IV. Methods of Inhibiting Cell Proliferation and Treating Cancer (E)-1-(pyridyn-4-yl)-3-(7-(trifluoromethyl)quinolin-2-yl)-prop-2-en-1-one (PFK-158) and compositions including the compound are useful for inhibiting cell proliferation and/or treating cancer.

In some embodiments, the methods for inhibiting cell proliferation or treating a cancer comprise administering to a subject in need thereof the anti-cancer compound PFK-158 as described herein. The active compound, as set forth above, includes the compound and its pharmaceutically acceptable salts. In some embodiments, the active compound is present in a pharmaceutical formulation as described hereinabove.

The presently disclosed compound can provide therapy for a wide variety of tumors and cancers including, but not limited to, glioblastoma multiforme, skin cancers, connective tissue cancers, adipose cancers, breast cancers, lung cancers, stomach cancers, pancreatic cancers, ovarian and reproductive organ cancers, cervical cancers, uterine cancers, anogenital cancers, kidney cancers, bladder cancers, liver cancers, colorectal or colon cancers and digestive (GI) tract cancers, prostate cancers and reproductive organ cancers, central nervous system (CNS) cancers, retinal cancer, blood, and lymphoid cancers, and head and neck cancers.

An "effective amount" as defined herein in relation to the treatment of cancers is an amount that will decrease, reduce, inhibit, or otherwise abrogate the growth of a cancer cell or tumor. In some embodiments, the compound described herein can be delivered regionally to a particular affected region or regions of the subject's body. In some embodiments, wherein such treatment is considered more suitable, the compound can be administered systemically. For example, the compound can be administered intravenously.

In addition, it will be appreciated that therapeutic benefits for the treatment of cancer can be realized by combining treatment with one or more additional anti-cancer agents or treatments. The choice of such combinations will depend on various factors including, but not limited to, the type of disease, the age and general health of the subject, the aggressiveness of disease progression, and the ability of the subject to tolerate the agents that comprise the combination.

Thus, a variety of chemical compounds, also described as "anti-cancer agents" or "chemotherapeutic agents" can be used in combination with PFK-158. Such compounds include, but are not limited to, alkylating agents, DNA intercalators, protein synthesis inhibitors, inhibitors of DNA or RNA synthesis, DNA base analogs, topoisomerase inhibitors, anti-angiogenesis agents, and telomerase inhibitors or telomeric DNA binding compounds. For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin.

Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, including alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents, such as distamycin and netropsin, also can be combined with PFK-158 in pharmaceutical compositions. Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be combined with the PFK-158 to provide a suitable cancer treatment.

Thus, current anti-cancer agents that can be used in a combination treatment with PFK-158 include, but are not limited to, adrimycin, 5-fluorouracil (5FU), etoposide, camptothecin, actinomycin-D, mitomycin, cisplatin, hydrogen peroxide, carboplatin, oxaliplatin, procarbazine, mechlorethamine, cyclophosphamide, ifosfamide, melphalan, chlorambucil, bisulfan, nitrosurea, dactinomycin, duanorubicin, doxorubicin, bleomycin, plicomycin, tamoxifen, paclitaxel, docetaxel, transplatimun, vinblastine, vincristine, methotrexate, irinotican, leucovorin, bevacizumab, cetuximab, sutinibib, imatinib, temozolomide, gemcitabine, and the like.

Combination treatments involving the compound of the present invention can be tested and another therapeutic agent, such as another chemotherapeutic agent can be achieved by using both agents at substantially the same time. Alternatively, treatment with the compound of the present invention can precede or follow treatment with the other agent by intervals ranging from minutes to weeks.

One mode of administration of chemotherapeutic agents is by parenteral administration, which requires solubility of the agent in solvents suitable for parenteral administration. Non-limiting examples of suitable solvents or solvent mixtures include Cremophor, Tween, polyethylene glycol, and/or polypropylene glycol in combination with parenteral solutions such as saline (0.9% sodium chloride in water for injection), D5W or D10W (5% or 10% respectively, glucose or dextrose in water for injection), and lactate Ringer's.

Accordingly, in one embodiment, a compound for the treatment of cancer, consisting of (E)-1-(pyridyn-4-yl)-3-(7-(trifluoromethyl)quinolin-2-yl)-prop-2-en-1-one, or a pharmaceutically acceptable salt thereof is provided, the compound having the formula:

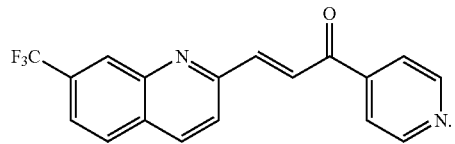 [SMILES: O=C(/C=C/c1ccc2ccc(C(F)(F)F)cc2n1)c1ccncc1]

In another embodiment, a pharmaceutical composition for the treatment of cancer is provided, comprising: (a) an effective amount of (E)-1-(pyridyn-4-yl)-3-(7-(trifluoromethyl)quinolin-2-yl)-prop-2-en-1-one or a pharmaceutically acceptable salt thereof; and (b) at least one pharmaceutically acceptable carrier. In a further embodiment, the composition additionally comprises a second anti-cancer agent. In certain embodiments, the second anti-cancer agent is selected from the group consisting of paclitaxel, docetaxel, cis-platin, carboplatin, oxaliplatin, doxorubicin, vincristine, vinblastine, 5-FU, irinotican, methotraxate, leucovorin, bevacizumab, cetuximab, sutinibib, imatinib, temozolomide, and gemcitabine. Such pharmaceutical compositions are useful in the treatment of various cancers treatable by inhibition of PFKFB3, including glioblastoma multiforme, skin cancers, connective tissue cancers, adipose cancers, breast cancers, lung cancers, stomach cancers, pancreatic cancers, ovarian and reproductive organ cancers, cervical cancers, uterine cancers, anogenital cancers, kidney cancers, bladder cancers, liver cancers, colorectal or colon cancers and digestive (GI) tract cancers, prostate cancers and reproductive organ cancers, central nervous system (CNS) cancers, retinal cancer, blood, and lymphoid cancers, and head and neck cancers.

In another embodiment, a method of treating cancer is provided, the method comprising administering to a subject in need thereof an effective amount of (E)-1-(pyridyn-4-yl)-3-(7-(trifluoromethyl)quinolin-2-yl)-prop-2-en-1-one or a pharmaceutically acceptable salt thereof. The method is useful in the treatment of various cancers treatable by inhibition of PFKFB3, including glioblastoma multiforme, skin cancers, connective tissue cancers, adipose cancers, breast cancers, lung cancers, stomach cancers, pancreatic cancers, ovarian and reproductive organ cancers, cervical cancers, uterine cancers, anogenital cancers, kidney cancers, bladder cancers, liver cancers, colorectal or colon cancers and digestive (GI) tract cancers, prostate cancers and reproductive organ cancers, central nervous system (CNS) cancers, retinal cancer, blood, and lymphoid cancers, head and neck cancers, and the like. In a further embodiment, the method additionally comprises administering a second anti-cancer agent. In specific embodiments, the second anti-cancer agent is selected from the group consisting of paclitaxel, docetaxel, cis-platin, carboplatin, oxaliplatin, doxorubicin, vincristine, vinblastine, 5-FU, irinotican, methotraxate, leucovorin, bevacizumab, cetuximab, sutinibib, imatinib, temozolomide, and gemcitabine. The second anti-cancer agent can be co-administered with (E)-1-(pyridyn-4-yl)-3-(7-(trifluoromethyl)quinolin-2-yl)-prop-2-en-1-one, or can be administered before or after (E)-1-(pyridyn-4-yl)-3-(7-(trifluoromethyl)quinolin-2-yl)-prop-2-en-1-one.

In another embodiment, a method of treating a tumor is provided, the method comprising administering to a subject in need thereof an effective amount of (E)-1-(pyridyn-4-yl)-3-(7-(trifluoromethyl)quinolin-2-yl)-prop-2-en-1-one or a pharmaceutically acceptable salt thereof. In a further embodiment, the method additionally comprises administering a second anti-cancer agent. In specific embodiments, the second anti-cancer agent is selected from the group consisting of paclitaxel, docetaxel, cis-platin, carboplatin, oxaliplatin, doxorubicin, vincristine, vinblastine, 5-FU, irinotican, methotraxate, leucovorin, bevacizumab, cetuximab, sutinibib, imatinib, temozolomide, and gemcitabine. The second anti-cancer agent can be co-administered with (E)-1-(pyridyn-4-yl)-3-(7-(trifluoromethyl)quinolin-2-yl)-prop-2-en-1-one, or can be administered before or after (E)-1-(pyridyn-4-yl)-3-(7-(trifluoromethyl)quinolin-2-yl)-prop-2-en-1-one.

In still another embodiment, a method of inhibiting glycolytic flux in a cell is provided, the method comprising contacting the cell with an effective amount of (E)-1-(pyridyn-4-yl)-3-(7-(trifluoromethyl)quinolin-2-yl)-prop-2-en-1-one or a pharmaceutically acceptable salt thereof.

In another embodiment, a method of inhibiting enzymatic activity of PFKFB3 in a cell is provided, the method comprising contacting the cell with an effective amount of (E)-1-(pyridyn-4-yl)-3-(7-(trifluoromethyl)quinolin-2-yl)-prop-2-en-1-one or a pharmaceutically acceptable salt thereof.

These and other embodiments will be further understood in light of the following Examples.

EXAMPLES

The following examples are given by way of illustration only and are not intended to limit the scope of the present invention.

Example 1

Inhibition of Cancer Cell Proliferation

The ability of PFK-158 to kill or inhibit the proliferation of cancer cells was measured using either the MTT assay, the AlamarBlue® assay (Invitrogen, Grand Island, N.Y.), or the CellTiter Glo™ assay (Promega, Madison, Wis.) using 48 or 72 hours exposure. MTT assay results for different cancer cell lines are shown in Table 5 below and demonstrate that PFK-158 inhibits cancer cell proliferation at low nanomolar concentrations across several types of cancer cell lines.

Cells of the desired tumor cell line were plated at $2 \times 10^5$ cells/ml in 96 well plates. Twice the indicated concentrations of the compounds of the invention were added to cells the following day in an equal volume of media. 72 hours later, cells were lysed and subjected to ATP determination using the CellTiter-Glo™ Luminescent Cell Viability Assay kit. Experiments were performed in triplicate. When using the MTT assay or the AlamarBlue® assay, the experimental conditions are essentially similar; at the end of the incubation period, 20 microliters of the MTT solution is added per well and the samples are incubated for an additional four hours, rinsed, and absorbance at 570 nm was measured. Results for the inhibition of cell proliferation are reported as the IC50 (the concentration resulting in 50% inhibition of proliferation of the cell population) and are listed in Table 5 below. Cell lines include lung, colon, prostate, breast, ovarian, and pancreatic cancer lines.

TABLE 5

$IC_{50}$ values for PFK-158 (MTT assay, 48 hours) in a panel of cell lines.

| Cell line | $IC_{50}$ (nM) |
|---|---|
| A498 | 3512 |
| A549 | 8654 |
| HCT116 | 3399 |
| HT29 | 4134 |
| MiaPaCa-2 | 3353 |
| SKOV-3 | 2625 |
| SW620 | 2668 |
| PC-3 | 1180 |
| BT474 | 1952 |
| SK-BR-3 | 1598 |

Example 2

Inhibition of Recombinant PFKFB3, PFKFB3 in Cells, and Glucose Uptake in Cells

The inducible bifunctional 6-Phosphofructo-2-kinase/fructose2,6-biphosphatase enzyme (PFKFB3) was expressed and purified in order to determine if PFK-158 inhibits enzymatic activity. PFKFB3 was prepared by expression in *E. coli* and purified by GST column and column chromatography. SDS Page coumassie staining gels indicated that purity was high (>95%). The recombinant protein was pure and active as determined by the results of a commercially available kinase activity assay (ADP-Glo™, Promega, Madison, Wis.). The same assay was used to determine inhibition of the protein and results are shown in FIG. 1, representing the inhibitory curve for PFK-158 resulting in an $IC_{50}$ of 137±15 nM.

Figure 3:
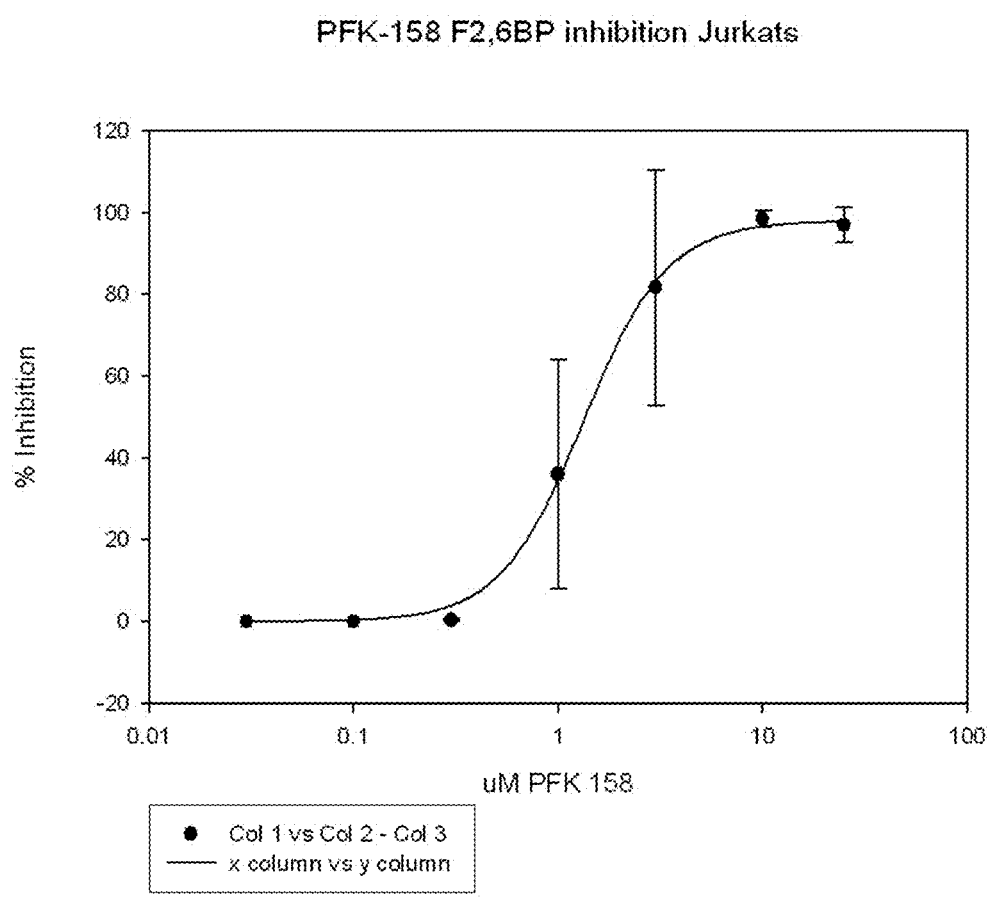
FIG. 3 shows inhibition of enzymatic activity of PFKFB3 in Jurkat cells by measurement of F2,6BP levels vs. concentration for PFK-158.

Inhibition of PFKFB3 can also be measured in cells by measuring fructose-2,6-biphosphate levels according to the Van Schaftingen method (*Eur. J. of Biochem*, 129: 191 (1982)). This method enables measurement of the inhibition in a cellular environment, a model more relevant than the pure recombinant protein. Briefly, Jurkat cells were plated at $1 \times 10^5$ cells/mL and incubated with different concentrations of PFK-158 for 3 hours. Samples were collected and cells were lysed. Extracts were characterized as described in previous reports and normalized to protein concentration. Results show that PFK-158 has an $IC_{50}$ of 1.6±0.8 µM. See FIG. 3.

Figure 2:
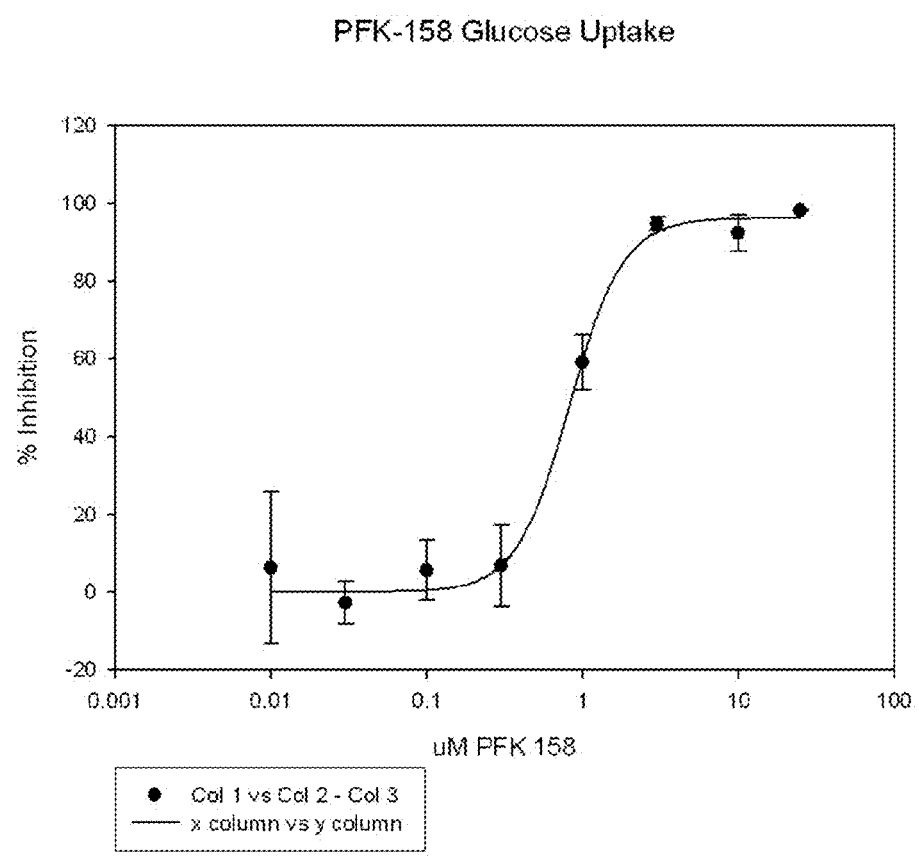
FIG. 2 shows inhibition of $^{14}C$ 2 deoxyglucose uptake by Jurkat cells vs. concentration for PFK-158.

Inhibition of PFKFB3 results in inhibiting glycolysis. Several feedback or feedforward activation and inhibition mechanisms exist so that, by a feedback mechanism, inhibiting the activity of PFKFB3 might inhibit glucose uptake by cells. An assay was developed to determine if there was inhibition of glucose uptake following exposure PFK-158. Briefly, Jurkat cells were plated at $10^5$ cells/mL in RPMI 1640 supplemented with 10% fetal bovine serum and 50 µg/mL gentamicin sulfate. Cells were immediately treated with vehicle or 0.5 µmol/L of PFK-158 for 3 hours and subsequently placed in glucose-free RPMI 1640 for 30 min. $^{14}C$-2-deoxyglucose (0.25 µCi/mL; Perkin Elmer) was added for an additional 60 min and cells were then washed three times with ice-cold RPMI 1640 containing no glucose. Cell lysates were collected in 500 µL of 0.1% SDS and scintillation counts (counts/min) were measured on 400 µL of lysate. Counts were normalized to protein concentration. The results indicate that PFK-158 has an $IC_{50}$ of 847±150 nM. See FIG. 2.

These results confirmed that the compound of the invention is a potent inhibitor of PFKFB3 and has low nanomolar $IC_{50}$s as summarized in Table 6 below.

TABLE 6

| $IC_{50}$ (nM) for PFK-158 (Jurkat cells) | | | |
|---|---|---|---|
| Rec PFKFB3 | Cellular PFKFB3 (F2, 6BP) | Glucose Uptake | Cell Growth |
| 137 ± 15 | 1620 ± 400 | 847 ± 150 | 328 ± 15 |

Example 3

Pharmacokinetics

The pharmacokinetic (PK) parameters for PFK-158 were determined in mice following IV (intravenous) administration in mice and rats. A typical study design includes six animals (male or female) 7 to 8 weeks old.

Figure 4:
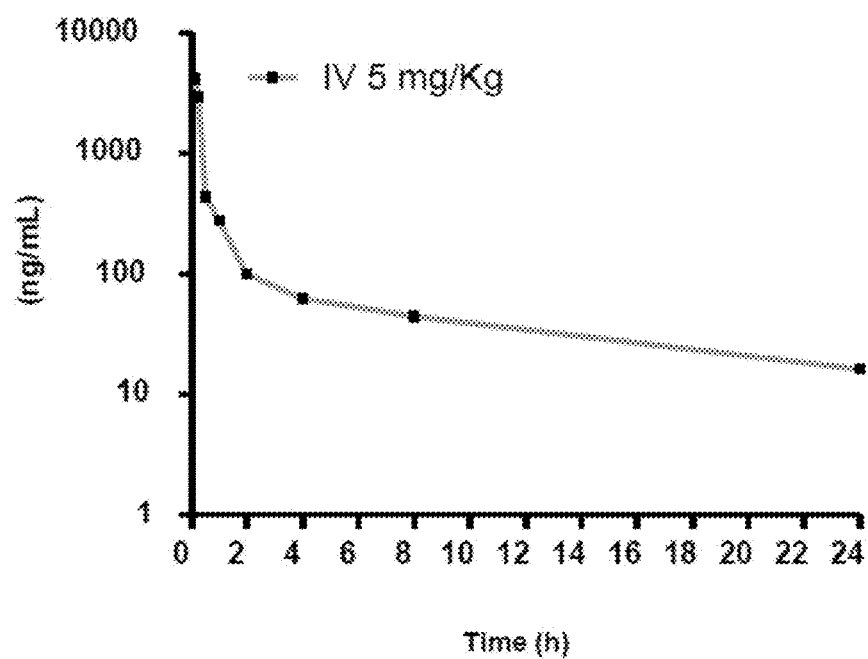
FIG. 4 shows the time vs. plasma concentration pharmacokinetic profile of PFK-158 in BalbC mice (IV dosing, 5 mg/kg).
Figure 5:
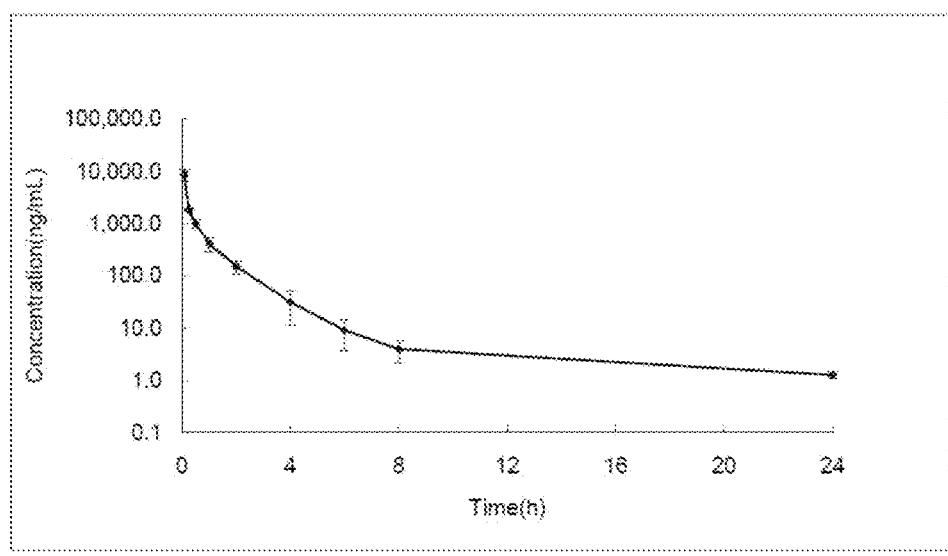
FIG. 5 shows the time vs. plasma concentration pharmacokinetic profile of PFK-158 in SD rats (IV dosing, 30 mg/kg).

Mouse pharmacokinetic properties using a dose of 5 mg/kg were determined after IV administration using a 10% DMSO, 10% PEG-200, 10% Solutol:ethanol (1:1) and 70% D5W solution or any other pharmaceutically acceptable parenteral formulation. Blood samples were collected at different intervals. Plasma samples were extracted and analyzed using an LC-MS/MS method. Similar protocols were used for the rat PK study (Sprague Dawley rats; 30 mg/kg), although the formulation for rat PK studies differed (30% Captisol, pH 3.0 solution). Time vs. plasma concentration plots were prepared as shown in FIG. 4 (BalbC mice) and 5 (SD rats), respectively. Pharmacokinetic parameters were calculated and are provided below in Table 7.

TABLE 7

| PK parameters (IV dosing; 5 mg/kg in Balbc mice; 30 mg/kg in Sprague Dawley rats). | | | |
|---|---|---|---|
| | $T_{1/2b}$ (h) | $C_{max}$ (ng/mL) | $AUC_{0-inf}$ (ng · h/ml) |
| Mouse (5 mg/kg) | 10.4 | 4,176 | 3,235 |
| Rat (30 mg/kg) | 8.6 | 18,883 | 3,298 |

Results show that the compound of the invention has a reasonably long half-life that supports exposure over a long period of time, a high maximum concentration, and high AUC, which support high drug concentration and exposure.

Example 4

Efficacy Studies

Efficacy of PFK-158 was studied in vivo in tumor models. Several tumor models were used in these studies (the Lewis lung carcinoma, or LLC model, the CT-26 colon carcinoma tumor model, or the BXPC3 pancreatic cancer model). The experimental protocol for the LLC study is described below. Subsequent to subcutaneous inoculation of tumor cells, tumors started to develop and once tumors reached the desired volume of 100-125 mm³ on average, treatment was initiated. Tumor volume was monitored in both groups and the average for both the control and treatment groups was measured three times a week, as well as body weights.

Figure 6:
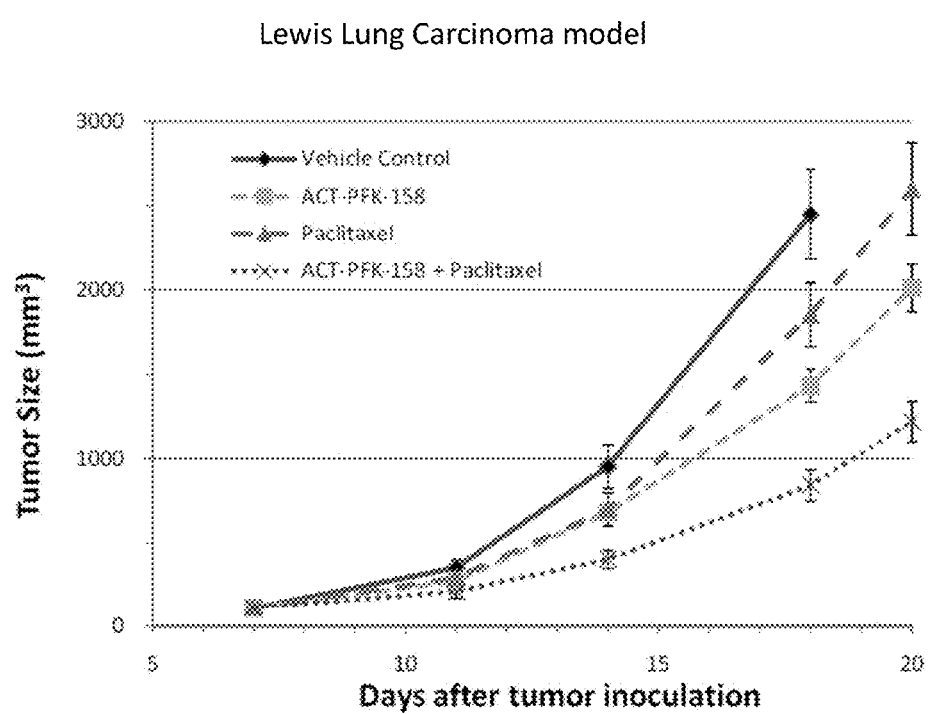
FIG. 6 shows average tumor volume as a function of time for control and treatment groups in the Lewis lung carcinoma model (LLC).

Briefly, normal female C57BL/6 mice at 7-8 weeks of age were used for the study. Mice were housed in microisolator housing, with food and water provided as libitum, and quarantined for 4 days prior to the initiation of the study. LLC cells were maintained in a monolayer culture in DMEM medium supplemented with 10% heat inactivated fetal calf serum, 100 U/ml penicillin and 100 µg/ml streptomycin, and L-glutamine (2 mM) at 37° C. in an atmosphere of 5% $CO_2$ in air. The tumor cells were routinely sub-cultured twice a week. The cells growing in an exponential phase were harvested and counted for tumor inoculation. Each mouse was inoculated subcutaneously at the right flank with the LLC tumor cells ($3\times10^5$) in 0.1 ml of PBS for tumor development. When athymic nude mice were used, as for the BxPC3 model, then the strain of mice is slightly different. Furthermore, the use of Matrigel supports tumor development, meaning that cells are suspended in 100 µl of a mixture of medium/Matrigel (1:1) and are then subcutaneously implanted in the right flank region. Animals were monitored for tumor growth daily after cell implantation. When tumor volumes reached approximately 100-125 mm³, mice were randomized into groups of 8 mice each using only mice having tumor volumes closest to the mean value. Tumor volumes were measured using the formula $V=L\times W\times H\times\pi/6$, where L and W represent the longer and shorter diameters of the tumor and H represents the height of the tumor. Treatment began following randomization. PFK-158 was administered IP at a dose of 60 mg/kg on days 1, 3, 5, 7, 9, 11, and 13. Animals were observed for possible toxic effect from the drug treatment. Body weights were recorded and showed that the compound was very well tolerated, with no noticeable body weight loss. Results are shown in FIG. 6.

Figure 7:
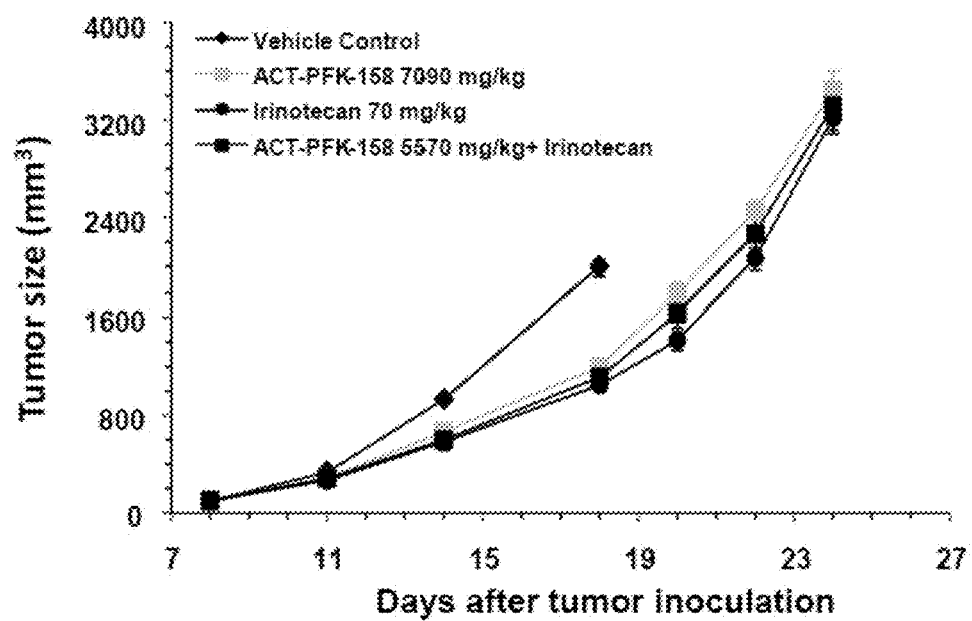
FIG. 7 shows average tumor volume as a function of time for control and treatment groups in the CT-26 murine colon cancer syngeneic model.
Figure 8:
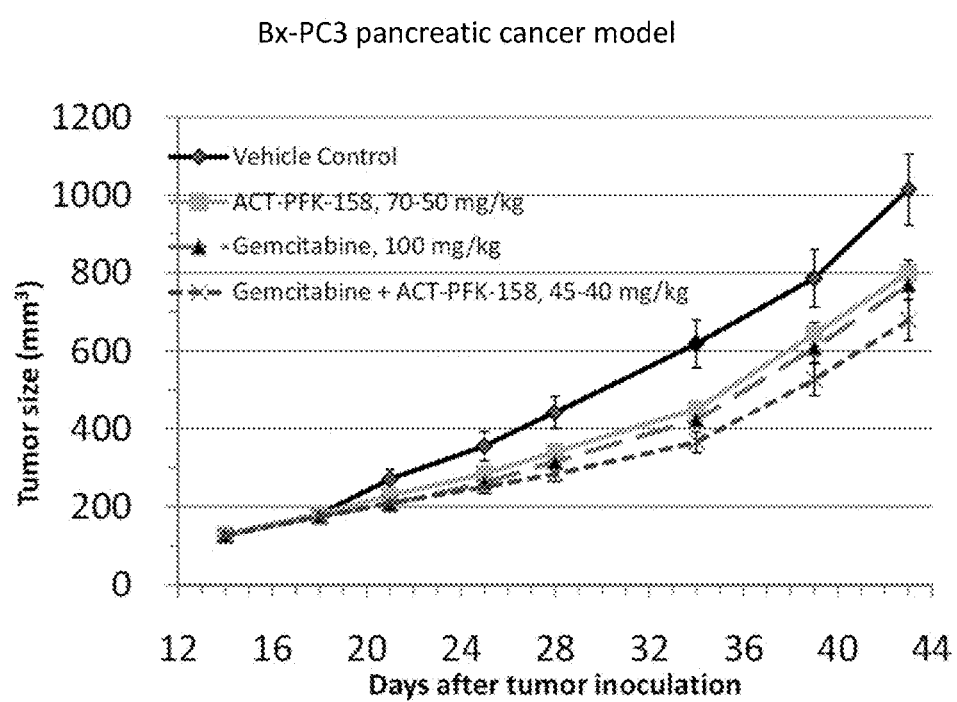
FIG. 8 shows average tumor volume as a function of time for control and treatment groups in the Bx-PC3 pancreatic cancer xenograft model.

Similar protocols were used for the other studies using different models; differences included the use of Balbc/nude mice; administering larger number of cancer cells; and use of Matrigel. Results of several studies are shown in FIGS. 6-8 and demonstrate that the compound of the invention inhibits tumor growth in vivo in different tumor types, while being very well tolerated, with no observable body weight loss nor animal death. Further, an additive or synergistic effect was observed when PFK-158 is combined with other chemotherapeutic agents.

Example 5

Comparison of PFK-158 to Quinolyl-Propenone Compounds

The same methods detailed in Table 1 above were used to compare PFK-158 to five structurally similar quinolyl-propenone compounds, bearing functional groups on the PFK-015 scaffold: 1-Pyridin-4-yl-3-(quinolin-2-yl)-propenone, 3-(6-methoxy-quinolin-2-yl)-1-pyridin-4yl-propenone (PFK-138), 1-(2-methoxy-pyridin-4-yl)-3-(6-methoxy-quinolin-2-yl)-propenone (PFK-144), 3-(6-(2-piperidin-1-yl-ethoxy)-quinolin-2-yl)-1-pyridin-4-yl-propenone (PFK-150), 1-Pyridin-4-yl-3-(8-trifluoromethyl-quinolin-2-yl)-propenone (PFK-153), and 3-(7-Methyl-quinolin-2-yl)-1-pyridin-4-yl-propenone (PFK-154).

Results show PFK-158 exhibits superior in vitro inhibition of PFKFB3 and 2 deoxyglucose and superior efficacy against Jurkat cells, when compared to each of the listed quinolyl-propenone variants of PFK-015. In many instances, PFK-158 showed a two- to six-fold improved performance in comparison to the tested compounds. See Table 8, below.

TABLE 8

IC$_{50}$ comparison of PFK-158 to quinolyl-propenone compounds

| Compound | IC$_{50}$, Enzymatic activity of PFKFB3, ADP-Glo ™ Assay | IC$_{50}$, Enzymatic activity of PFKFB3 in cells | IC$_{50}$, Inhibition of 2 deoxyglucose uptake | IC$_{50}$, toxicity of Jurkat cell line (leukemia cell line) |
|---|---|---|---|---|
| 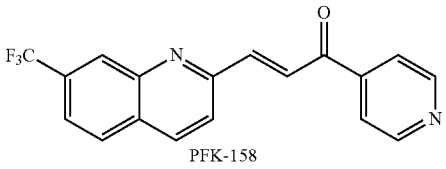 PFK-158 | 137 ± 15 nM | 1.6 ± 0.8 μM | 0.8 ± 0.1 μM | 0.33 ± 0.1 μM |
| 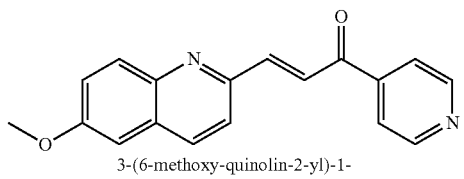 3-(6-methoxy-quinolin-2-yl)-1-pyridin-4yl-propenone (PFK-138) | 431 ± 34 nM | 7.4 ± 1.8 μM | 2.2 ± 0.3 μM | 1.2 ± 0.2 μM |
| 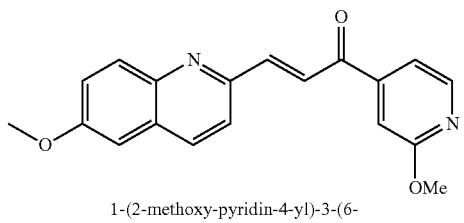 1-(2-methoxy-pyridin-4-yl)-3-(6-methoxy-quinolin-2-yl)-propenone (PFK-144) | 654 ± 94 nM | 10.7 ± 0.3 μM | 3.1 ± 0.5 μM | 1.7 ± 0.3 μM |
| 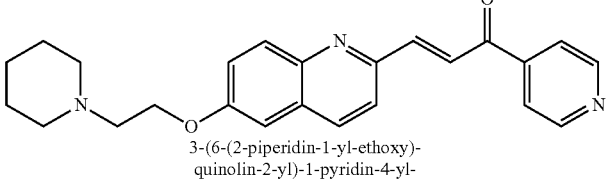 3-(6-(2-piperidin-1-yl-ethoxy)-quinolin-2-yl)-1-pyridin-4-yl-propenone (PFK-150) | 802 ± 177 nM | 15.6 ± 1.4 μM | 3.8 ± 0.8 μM | 2.5 ± 0.4 μM |
| 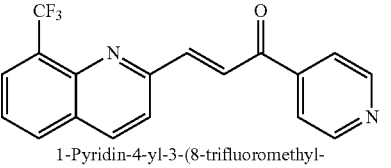 1-Pyridin-4-yl-3-(8-trifluoromethyl-quinolin-2-yl)-propenone (PFK-153) | 173 ± 23 nM | 6.0 ± 0.6 μM | 1.2 ± 0.6 μM | 0.9 ± 0.1 μM |
| 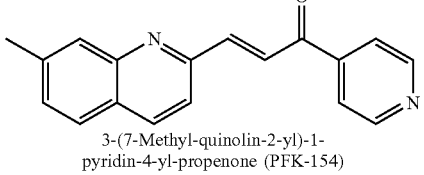 3-(7-Methyl-quinolin-2-yl)-1-pyridin-4-yl-propenone (PFK-154) | 622 ± 39 nM | 11.3 ± 0.6 μM | 2.2 ± 0.6 μM | 1.3 ± 0.1 μM |

Furthermore, PFK-158 also exhibits unexpected and superior pharmacokinetic properties, when compared to the tested compounds. As shown in Table 9, key pharmacokinetic parameters obtained in BalbC mice, such as $T_{1/2}$ (half-life), $C_{max}$ (maximum concentration), AUC (area under the curve), or Cl (clearance), show that PFK-158 exhibits unpredicted and superior pharmacokinetics compared to structurally similar quinolyl-propenones administered at the same concentration (IV dosing). PFK-158 exhibits a higher $C_{max}$ and AUC, longer half-life, and lower clearance compared to the tested compounds.

TABLE 9

Pharmacokinetic comparison of PFK-158 to quinolyl-propenone compounds

| Compounds | $T_{1/2}$ (hr) | $C_{max}$ (ng/ml) | $AUC_{0\text{-}Inf}$ (ng.h/mL) | Cl (mL/min/kg) |
|---|---|---|---|---|
| 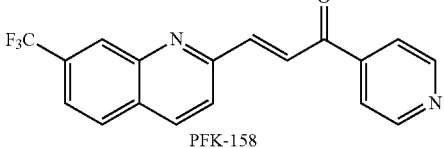<br>PFK-158 | 10.5 | 4176 | 3235 | 26 |
| 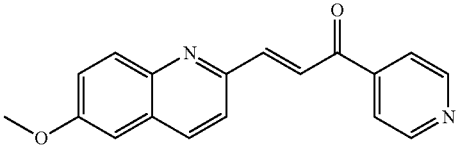 [SMILES: COc1ccc2nc(/C=C/C(=O)c3ccncc3)ccc2c1]<br>3-(6-methoxy-quinolin-2-yl)-1-pyridin-4yl-propenone (PFK-138) | 0.7 | 991 | 541 | 154 |
| 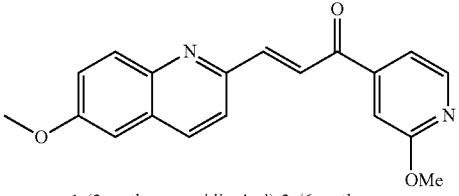<br>1-(2-methoxy-pyridin-4-yl)-3-(6-methoxy-quinolin-2-yl)-propenone (PFK-144) | 2.8 | 1504 | 696 | 120 |
| 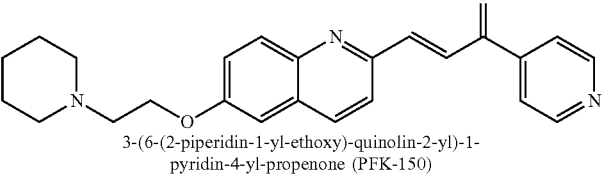<br>3-(6-(2-piperidin-1-yl-ethoxy)-quinolin-2-yl)-1-pyridin-4-yl-propenone (PFK-150) | 2.5 | 40 | 63 | 1327 |
| 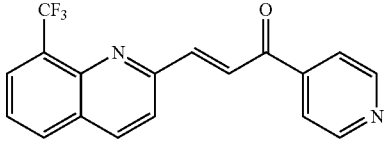 [SMILES: O=C(/C=C/c1ccc2cccc(C(F)(F)F)c2n1)c1ccncc1]<br>1-Pyridin-4-yl-3-(8-trifluoromethyl-quinolin-2-yl)-propenone (PFK-153) | 3.8 | 397 | 225 | 327 |
| 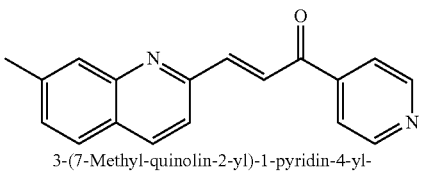<br>3-(7-Methyl-quinolin-2-yl)-1-pyridin-4-yl-pmpe none (PFK-154) | 6.1 | 672 | 1105 | 75 |

When taken together, the in vitro data and the in vivo pharmacokinetic data show that PFK-158 is surprisingly superior compared to the tested analogs. PFK-158 possesses a superior combination of in vitro cellular activity and in vivo pharmacokinetic properties; close analogs of PFK-158 do not possess the same level of activity against PFKFB3 and cancer cells in combination with the observed exceptional pharmacokinetic properties of PFK-158.

Example 6

Formulations for IV Administration

PFK-158 and its salts can be prepared in a Cremophor® based formulation. In one embodiment, 10 mg PFK-158 are dissolved in 1 ml of 1:1 v:v Cremophor®:ethyl alcohol solution using vigorous stirring. Once the compound is effectively dissolved, the solution is filtered and then added to saline, water for injection, lactate Ringer's, or D5W in a 1:9 ratio, resulting in a clear solution, free from particles, with a PFK-158 concentration of about 1 mg/ml. The composition is chemically stable for at least 6 hours and can be administered to mammals, including humans.

In another embodiment, a solution can be prepared with a salt of PFK-158, such as the chloride salt PFK-158, HCl. Similar formulations can be prepared with emulsifiers such as Tween 80® and the like.

In other embodiments, additional excipients are added to increase the concentration of PFK-158 or PFK-158, HCl. Suitable excipients include polyethylene glycol, polypropylene glycol, sodium carboxymethylcellulose, polyvinyl-pyrrolidone, and the like.

In another embodiment, an emulsion of PFK-158 is prepared on w/w basis: 1% PFK-158, 15% E80 (lipid based excipient), 5% soybean oil, 2% Polysorbate 80, 10% sucrose, 67% water, The pH is adjusted to 5.5 and then the composition is mixed well using any available high speed mixer. The resulting emulsion is stable and can be safely administered intravenously to mammals, including humans. In another embodiment, the emulsion comprises 0.5% PFK-158, 10% Soybean oil, 5.5% Miglyol 812, 5% PL90G, 10% Sucrose, and 69% DI water. The components are mixed and then emulsified using a high speed mixer. Many different excipients are suitable for use in the preparation of an emulsion as long as the required size, stability, and active concentration can be achieved.

In another embodiment, a solution containing a cyclodextrin can also be used to administer PFK-158 and its salts to cancer patients. In one embodiment, a solution of 30% w/v Captisol® in water for injection is prepared; then, the amount required to achieve a 5 mg/ml PFK-158, HCL solution is added and the solution stirred until complete dissolution is obtained and the pH is adjusted to 3.5. This solution can be safely administered to mammals, including humans. Optionally, the solution can be lyophilized. Addition of water for injection leads to complete re-dissolution of the lyophilate, at which point the solution is suitable for IV administration to a mammal.

Example 7

IV Pharmacokinetic Parameters in Rats and Dogs at 40 mg/kg

In another embodiment, a cyclodextrin based solution was used to investigate the PK profile of PFK-158, 2HCl at a higher concentration in both rats and dogs.

The solution was prepared with 40% w/v Captisol® in water for injection, 5% Mannitol, and a pH 2.3 citrate buffer leading to a 8 mg/ml concentration of PFK-158, 2HCl. This solution was safely administered IV to rats and dogs at a dose of 40 mg/kg. Blood samples were taken over a 24 hour period and analyzed. Plasma $AUC_{0 \to t}$ values of 37,600±2800 hr·ng/mL and 27,700±5800 hr·ng/mL, and plasma $C_{max}$ values of 51,400±6300 ng/mL and 39,500±10,000 ng/mL were calculated for male and female rats, respectively. Pharmacokinetic parameters were calculated in the same way in dogs: plasma $AUC_{0 \to 24}$ values of 16,100±700 and 15,900±2600 hr·ng/mL, and plasma $C_{5min}$ values of 6960±1180 and 6900±900 ng/mL were obtained for male and female dogs, respectively. Results showed high exposure in both species.

Example 8

Toxicology Study in Dogs at 40 mg/kg

In another embodiment, the potential toxicity of PFK-158 (in the form of its dication) was investigated at 40 mg/kg in male and female beagle dogs using a 3 day a week for a total of three weeks dosing regimen. The potential toxicity of PFK-158 was investigated by monitoring all clinical signs during the in-life phase, taking blood and urine samples for full clinical chemistry panels and urinalysis, monitoring body weights and food intake. Gross necropsy and complete histopathology were performed at the time of termination.

Results showed that, at the dose of 40 mg/kg dosed three times a week for three weeks, PFK-158 was very well tolerated and that there were no signs of toxicity. This dose was identified as the NOAEL (No Observable Adverse Events Level) and corresponds to the Human Equivalent Dose (HED) of 800 mg/m$^2$. As shown in Example 4 above, PFK-158 shows good activity in several cancer models at IV doses of 30 mg/kg or an HED of 90 mg/m$^2$. PFK-158 has therefore a wide therapeutic window that further supports its development.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

The invention claimed is:
1. A pharmaceutical composition comprising:
   (E)-1-(pyridyn-4-yl)-3-(7-(trifluoromethyl)quinolin-2-yl)-prop-2-en-1-one or a pharmaceutically acceptable salt thereof; and
   a cyclodextrin selected from the group consisting of sulfobutyl ether beta cyclodextrin and beta cyclodextrin.
2. The pharmaceutical composition of claim 1, wherein the cyclodextrin is sulfobutyl ether beta cyclodextrin.
3. The pharmaceutical composition of claim 1, further comprising mannitol.
4. The pharmaceutical composition of claim 1, wherein the pharmaceutical composition is an aqueous solution or a lyophilate.
5. An aqueous pharmaceutical composition comprising:
   (E)-1-(pyridyn-4-yl)-3-(7-(trifluoromethyl)quinolin-2-yl)-prop-2-en-1-one or a pharmaceutically acceptable salt thereof; and
   sulfobutyl ether beta cyclodextrin.
6. The aqueous pharmaceutical composition of claim 5, wherein the (E)-1-(pyridyn-4-yl)-3-(7-(trifluoromethyl)quinolin-2-yl)-prop-2-en-1-one or pharmaceutically acceptable salt thereof has a concentration of 5 mg/ml.
7. The aqueous pharmaceutical composition of claim 6, wherein the sulfobutyl ether beta cyclodextrin has a concentration of 30% w/v.
8. The aqueous pharmaceutical composition of claim 7, wherein the composition has a pH of 3.5.
9. The aqueous pharmaceutical composition of claim 7, wherein the composition has a pH of 3.0.

10. A lyophilized pharmaceutical composition comprising:
- (E)-1-(pyridyn-4-yl)-3-(7-(trifluoromethyl)quinolin-2-yl)-prop-2-en-1-one or a pharmaceutically acceptable salt thereof; and
- a cyclodextrin selected from the group consisting of sulfobutyl ether beta cyclodextrin and beta cyclodextrin.

11. The lyophilized pharmaceutical composition of claim 10, wherein the cyclodextrin is sulfobutyl ether beta cyclodextrin.

\* \* \* \* \*